US00PP25287P2

(12) United States Plant Patent
Klemm et al.

(10) Patent No.: US PP25,287 P2
(45) Date of Patent: Feb. 10, 2015

(54) ***CALIBRACHOA* PLANT NAMED 'KLECA12235'**

(50) Latin Name: ***Calibrachoa* sp.**
Varietal Denomination: KLECA12235

(71) Applicant: Klemm+Sohn GmbH & Co. KG, Stuttgart (DE)

(72) Inventors: Nils Klemm, Stuttgart (DE); Anita Stöver, Ostfildern (DE)

(73) Assignee: Klemm + Sohn GmbH & Co. KG, Stuttgart (DE)

( * ) Notice: Subject to any disclaimer, the term of this patent is extended or adjusted under 35 U.S.C. 154(b) by 59 days.

(21) Appl. No.: 13/987,404

(22) Filed: Jul. 22, 2013

(51) Int. Cl.
*A01H 5/00* (2006.01)

(52) U.S. Cl.
USPC ..... Plt./413

(58) Field of Classification Search
USPC ..... Plt./413
See application file for complete search history.

*Primary Examiner* — Kent L Bell
(74) *Attorney, Agent, or Firm* — James M. Weatherly; Cochran Freund & Young LLC

(57) ABSTRACT

A new *Calibrachoa* plant particularly distinguished by having a white flower color and a flat, trailing plant habit, is disclosed.

1 Drawing Sheet

Genus and species: *Calibrachoa* sp.
Variety denomination: 'KLECA12235'.

BACKGROUND OF THE NEW PLANT

The present invention comprises a new and distinct variety of *Calibrachoa*, botanically known as *Calibrachoa* sp. and hereinafter referred to by the variety name 'KLECA12235'. 'KLECA12235' originated from an open-pollination between the proprietary female *Calibrachoa* variety 'CA 08 0011' (unpatented) and an unknown male *Calibrachoa* variety.

In May 2008, two *Calibrachoa* parental lines, 'CA 08 0011' and an unknown *Calibrachoa* were open-pollinated in Stuttgart, Germany and seeds were obtained. The seeds were sown and plants were grown for evaluation. A plant line was selected in May 2009 and subsequently named 'KLECA12235'. In May 2009, 'KLECA12235' was first vegetatively propagated by tip cuttings. 'KLECA12235' was found to reproduce true to type in successive generations of asexual propagation via tip cuttings.

CROSS REFERENCE TO RELATED APPLICATIONS

Plant Breeder's Rights for 'KLECA12235' were applied for in Canada on Jan. 23, 2013, Application No. 13-7850 and in Switzerland on Jun. 6, 2013, Application No. 13-2871. 'KLECA12235' has not been made publicly available or sold more than one year prior to the filing date of this application.

SUMMARY

The following are the most outstanding and distinguishing characteristics of this new variety when grown under normal horticultural practices in Stuttgart, Germany.

1. White flower color; and
2. A flat, trailing plant habit.

DESCRIPTION OF THE PHOTOGRAPH

This new *Calibrachoa* plant is illustrated by the accompanying photograph which shows a close-up of the flowers. The photograph is of a five-month-old plant grown in a controlled greenhouse environment in Stuttgart, Germany in May 2012. The colors shown are as true as can be reasonably obtained by conventional photographic procedures.

DESCRIPTION OF THE NEW VARIETY

The following detailed descriptions set forth the distinctive characteristics of 'KLECA12235'. The data which define these characteristics were collected from asexual reproductions carried out in Stuttgart, Germany. Data was collected on five-month old plants grown in Stuttgart, Germany in May 2013. Color references are to The R.H.S. Colour Chart of The Royal Horticultural Society of London (R.H.S.), 5$^{th}$ edition (2007).

Classification:
- *Family*.—Solanaceae.
- *Species*.—*Calibrachoa* sp.
- *Common name*.—*Calibrachoa*.

Parentage:
- *Female*.—Proprietary *calibrachoa* plant 'CA 08 0011'.
- *Male*.—An unknown male *calibrachoa* plant.

Plant description:
- *Life cycle*.—Annual.
- *Form*.—Flat, trailing.
- *Habit*.—Trailing.
- *Height (from soil line to top of foliage)*.—5.0 cm.
- *Spread*.—41.0 cm.

Propagation: Vegetatively propagated.
- *Type cuttings*.—Tip cuttings.
- *Time to produce a rooted cutting*.—3 weeks.

Stems:
- *Stem diameter*.—7.0 cm.
- *Stem length*.—19.0 cm. From soil line to first node: 1.2 cm. Total length: 21.0 cm.
- *Internode length*.—1.2 cm.
- *Stem color*.—RHS 145A.
- *Pubescence*.—Absent.

Leaves:
*Arrangement*.—Alternate, simple, sessile.
*Shape*.—Elliptic.
*Apex*.—Obtuse to slightly acute.
*Base*.—Attenuate.
*Margin*.—Entire.
*Surface*.—Smooth.
*Surface pubescence*.—Absent.
*Venation*.—Pinnate.
*Venation color*.—Upper surface: RHS 145A. Lower surface: RHS 146D.
*Length*.—2.4 cm.
*Width*.—0.6 cm.
*Color*.—Upper surface: RHS 144A. Lower surface: RHS 144B.
*Fragrance*.—Absent.
Flowers: Single flowers.
*Flowering habit*.—Flower attitude semi-erect, single, axillary.
*Flower type*.—Determinate inflorescence.
*Flowering requirements*.—A minimum of light sun is required.
*Duration of flowers*.—5 days.
*Corolla*.—Smooth texture.
*Shape*.—Funnel-shaped.
*Fragrance*.—Absent.
Flower buds:
*Surface*.—Smooth.
*Length*.—1.5 cm.
*Diameter*.—0.6 cm.
*Shape*.—Irregular to oblong.
*Color*.—RHS 154D.
Peduncle:
*Length*.—1.3 cm.
*Diameter*.—0.1 cm.
*Color*.—RHS 145B.
*Texture*.—Smooth.
*Anthocyanin color*.—RHS 178C.
Flower description:
*Flower depth*.—2.8 cm.
*Flower tube length*.—2.0 cm.
*Flower tube diameter*.—0.7 cm.
*Flower diameter*.—3.3 cm.
*Pedicel color*.—RHS 145B.
*Calyx*.—Funnel-shaped.
Sepals:
*Shape*.—Lanceolate.
*Apex*.—Acute.
*Margin*.—Entire.
*Length*.—1.3 cm.
*Diameter*.—0.3 cm.
*Sepal color*.—Upper surface: RHS 144C. Lower surface: RHS 146D.
Petals:
*Shape*.—Heart-shaped.
*Length*.—1.8 cm.
*Apex*.—Obverse.
*Margin*.—Entire, weak undulation.
*Base*.—Open and fused into the tube.
*Pubescence*.—Absent.
*Lobe length*.—1.7 cm.
*Lobe width*.—1.4 cm.
*Color*.—Lobe color: Upper surface: RHS NN155D. Lower surface: RHS NN155D. Corolla tube color: Inner: RHS 154C. Outer: RHS 154D.
*Fragrance*.—Absent.
Reproductive organs:
*Stamen number*.—5.
*Stamen color*.—Anther color: RHS 13B. Filament color: RHS 1C. Pollen color: RHS 13B.
*Ovary*.—Placenta arrangement: Ovate. Pistil number: 1. Pistil length: 0.1 cm. Stigma color: RHS 154B. Style length: 0.9 cm. Style color: RHS 151B.
Fruit/seed set: Little seed production.
Disease/insect resistance: None observed.

COMPARISON WITH PARENTAL LINE AND KNOWN VARIETY

'KLECA12235' is distinguished from its female parent as described in Table 1:

TABLE 1

Comparison with Parental Line

| Trait | Variety 'KLECA12235' | Female parent 'CA 08 0011' |
|---|---|---|
| Growing habit | Flat, trailing | Upright |

'KLECA12235' is most similar to the *Calibrachoa* plant named 'KLECA06122' (U.S Plant Pat. No. 19,477). Differences between the two varieties are described in Table 2:

TABLE 2

Comparison with Similar Variety

| Trait | Variety 'KLECA12235' | Commercial line 'KLECA06122' |
|---|---|---|
| Growing habit | Flat, trailing | Upright to semi-trailing |

We claim:

1. A new and distinct variety of *Calibrachoa* plant named 'KLECA12235' as illustrated and described herein.

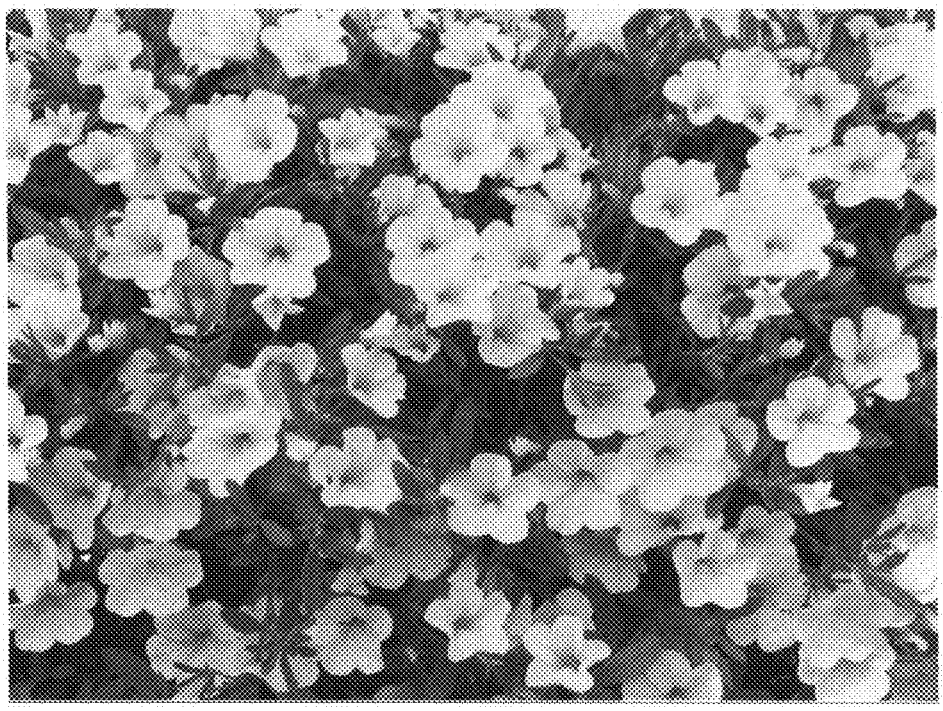

* * * * *